United States Patent [19]

Lippa

[11] Patent Number: 6,162,463
[45] Date of Patent: Dec. 19, 2000

[54] EXTENDED RELEASE FORMULATION OF DILTIAZEM HYDROCHLORIDE

[76] Inventor: Arnold S. Lippa, 185 Prospect #3M, Hackensack, N.J. 07601

[21] Appl. No.: 09/067,573

[22] Filed: Apr. 28, 1998

Related U.S. Application Data

[60] Provisional application No. 60/046,989, May 1, 1997.
[51] Int. Cl.$^7$ .................................................. A61K 9/48
[52] U.S. Cl. ........................ 424/451; 424/489; 424/470; 424/457; 424/468; 424/464; 424/456; 424/400
[58] Field of Search .................................... 424/451, 489, 424/490, 497, 473, 468; 525/217

[56] References Cited

U.S. PATENT DOCUMENTS

| | | | |
|---|---|---|---|
| 4,894,240 | 1/1990 | Geoghegan et al. | 424/497 |
| 5,028,664 | 7/1991 | Ohmura et al. | 525/217 |
| 5,252,338 | 10/1993 | Jao et al. | 424/473 |
| 5,472,710 | 12/1995 | Klokkens-Bethke et al. | 424/468 |
| 5,578,322 | 11/1996 | Shiozawa et al. | 424/490 |

*Primary Examiner*—Thurman K. Page
*Assistant Examiner*—William E. Benston, Jr.

[57] ABSTRACT

An extended release formulation of diltiazem which is suitable for once-daily oral administration comprises a quantity of a quick release preparation of diltiazem or a pharmaceutically active salt thereof, mixed with a quantity of a slow release (or delayed release) preparation of diltiazem or a pharmaceutically active salt thereof. The quick release preparation used obtains a maximal release of diltiazem within approximately 1–2 hours after administration, and then falls toward baseline levels. The delayed release preparation individually shows a maximal release of diltiazem at between approximately 6–8 hours after administration. The formulation containing the two preparation achieves a maximal release of diltiazem approximately within 1–2 hours after administration, and the levels of released diltiazem remain near these maximal levels for approximately another 12 hours after administration, compared to other extended release formulations of diltiazem (referred to herein as slow or delayed release preparations) which achieve maximal release approximately 9 hours after oral administration. The preferred embodiment is a capsule containing the formulation, which, based upon the total quantity of drug in the formulation rather than total weight of the formulation, comprises up to approximately 25 percent by weight of the quick release preparation of diltiazem, and up to 75 percent by weight of the slow (or delayed) release preparation of diltiazem. The present invention has application for combinations of other preparations of quick release and slow or delayed release pharmaceuticals.

16 Claims, 6 Drawing Sheets

DILTIAZEM OD ER

DILTIAZEM XR

EXTENDED RELEASE FORMULATION OF DILTIAZEM HYDROCHLORIDE

CROSS-REFERENCE TO RELATED APPLICATIONS

This application claims the benefit of U.S. Provisional Application No. 60/046,989, filed May 1, 1997, for Extended Release Formulation of Diltiazem Hydrochloride.

STATEMENT REGARDING FEDERALLY SPONSORED RESEARCH OR DEVELOPMENT

Not Applicable.

REFERENCE TO A "MICROFICHE APPENDIX"

Not Applicable.

FIELD OF THE INVENTION

This invention relates to a formulation of diltiazem hydrochloride. In particular, this invention is an extended release formulation of diltiazem hydrochloride that is suitable for once daily use and which more rapidly achieves a maximum therapeutic level of diltiazem hydrochloride than that obtained with currently available formulations.

BACKGROUND OF THE INVENTION

Diltiazem ((2S-cis-3-(Acetoxyl)-5-[2-(dimethylamino)ethyl]-2-3-dihydro-2-(4-methoxyphenyl)-1,5-benzothiazepin-4(5H)-one) is a safe and effective treatment for both stable and unstable angina pectoris (1). A variety of formulations containing diltiazem or diltiazem hydrochloride are available, as will be described below. These formulations provide a range of dose regimens, ranging from dosing as often as four times daily ("q.i.d."); twice daily ("b.i.d."), such as approximately every 12 hour, or once-daily ("q.d."). Patient compliance with the dosing regimens has been a factor in the development of the sustained or extended release formulations, enabling the twice-daily or once-daily dosing.

CARDIZEM CD (TM) is a once-a-day extended release formulation of diltiazem hydrochloride sold by Marion Merrill Dow Corporation, Kansas City, Mo., and which is prescribed for treatment of hypertension and angina (2).

DILACOR XR (TM) is an extended release formulation of diltiazem hydrochloride sold by Rhone-Poulenc Rorer Pharmaceuticals, Inc., Collegeville, Pa. Capsules of DILACOR XR (TM) contain a controlled release formulation of diltiazem that is designed to release the drug over a 24 hour period, using a controlled release system marketed under the trademark GEOMATRIX (registered to Jago Research AG (Zollikon, Switzerland) (3).

Diltiazem OD ER (Once-a-Day, Extended Release as described in the literature) is an extended release formulation of diltiazem sold in the U.S. under the trade name TIAZAC (TM) by Forest Pharmaceuticals, Inc., St. Louis, Mo., and approved for treatment of hypertension (4).

Diltiazem hydrochloride is also commercially available in the powder form from chemical supply companies such as Sigma Chemical Corp., St. Louis, Mo.

Panoz et al. (including Geoghegen as a coinventor, see below) in U.S. Pat. No. 4,721,619 (the "'619 patent") describe a controlled absorption diltiazem formulation intended for twice daily usage. The formulation includes a core containing diltiazem, and a multi-layer membrane surrounding the core. The composition of the water insoluble and water soluble polymer mixture used in the membrane, and the number of layers of membrane surrounding the core, affect the release rate of the drug from the core over a twelve hour period following oral administration. Peak plasma levels were obtained approximately 9–12 hours after administration of the formulation described in the '619 patent.

Geoghegen et al., in U.S. Pat. Nos. 4,894,240; 4,917,899; 5,002,776; and 5,616,345 describe controlled absorption formulations for diltiazem, based upon the formulation described in the '619 patent. In U.S. Pat. No. 4,894,240 the formulation is designed for once-daily administration and provides maximal release of diltiazem approximately 10–14 hours after oral administration.

The formulation described in U.S. Pat. No. 4,917,899 is characterized by its maximum release of diltiazem approximately 9 hours after administration. This formulation includes a mixture of slow release and fast release pellets of diltiazem, the fast release pellets having a thinner coating than that of the slow release pellets.

Hendrickson et al., in U.S. Pat. No. 5,286,497 (the "'497 patent"), U.S. Pat. Nos. 5,439,689 and 5,470,584 describe a diltiazem formulation intended for once-daily administration. These formulations contain a mixture of two types of beads, described as a rapid release bead and a delayed release bead. As described in the '497 patent, when tested separately, the rapid release beads reach their maximal release of drug within 6–8 hours after oral administration, with the delayed release bead reaching its maximal release of drug within 16–24 hours post-administration. The beads contain a core comprising diltiazem and may contain conventional pharmaceutical excipients, while the coating of the beads is a polymer that envelopes or substantially envelopes the core, thereby effecting the controlled release characteristics of the drug from the core. As described in the '491 patent, this formulation follows a "stair step" pattern of drug release, achieving a first maximum level of drug release at approximately 6–8 hours, and a second maximal level of drug release after approximately 21 hours in in vitro dissolution tests. When administered to humans, the formulation achieved a maximum plasma level at approximately 6–8 hours post-administration, with plasma levels dropping slowly for the next ten hours.

In U.S. Pat. No. 5,508,040 Chen describes a multiparticulate pulsatile drug delivery system, containing a plurality of pellets or particles that are made up of two or more populations of pellets or particles. The particle populations each contain a core or bead containing the drug to be delivered, and a polymer film coating surrounding the core. The thickness of the coating surrounding the core controls the rate of release of the drug into its environment of use, such as the stomach. The result is a pulsatile manner of drug delivery: the drug is released from a first population of pellets over a time period of approximately 4.5 hours after administration, its maximum release occurring at approximately 3 hours, and falling to base line levels by 4.5 hours; the second population of pellets starts releasing drug at approximately 3 hours after administration, peaking out at approximately 6 hours, and falling to base line levels at approximately 7.5 hours, and in embodiments where a third population of pellets is contained in the formulation, the release of drug from the third population follows the same 4.5 hour distribution pattern as the first two particle populations, only the start of drug release is delayed. When shown graphically, the quantity of drug released as a function of time post-administration is characterized by rising and falling drug levels. Consequently, the curve shows both peaks and valleys as a function of time after administration, corresponding to the rising and falling levels of the released drug.

Studies have shown that angina attacks occur in a diurnal cycle, and their occurrence is common in the hours shortly after an individual commences activity after waking. These studies will be described further in the INTRODUCTION section of the Description of the Invention, below. In view of the fluctuations of drug levels observed, or the delay seen in obtaining peak drug levels, with certain extended release diltiazem formulations, and the short time between waking and the onset of angina attacks, there is a need for a diltiazem formulation that will rapidly achieve therapeutic drug levels, and maintain them over a prolonged period, thereby improving both clinical efficacy and patient compliance with the dosage regimen.

SUMMARY OF THE INVENTION

It is an object of the present invention to provide an extended release formulation of a pharmaceutically active compound or a pharmaceutically active salt thereof that can rapidly achieve a therapeutic concentration of the pharmaceutically active compound.

Another object of the present invention is to provide an extended release formulation of a pharmaceutically active compound or a pharmaceutically active salt thereof that can maintain a therapeutic concentration of the pharmaceutically active compound over a prolonged time period.

Yet another object of the present invention is to provide an extended release formulation of a pharmaceutically active compound or a pharmaceutically active salt thereof that is suitable for oral administration.

Still another object of the present invention is to provide an extended release formulation of a pharmaceutically active compound or a pharmaceutically active salt thereof that can be used once daily.

It is an object of the present invention to provide an extended release formulation of diltiazem or diltiazem hydrochloride that can rapidly achieve a therapeutic concentration of diltiazem.

Another object of the present invention is to provide an extended release formulation of diltiazem or diltiazem hydrochloride that can maintain a therapeutic concentration of diltiazem over a prolonged time period.

Yet another object of the present invention is to provide an extended release formulation of diltiazem or diltiazem hydrochloride is suitable for oral administration.

Still another object of the present invention is to provide an extended release formulation of diltiazem or diltiazem hydrochloride that can be used once daily.

The present invention is an extended release formulation of diltiazem (diltiazem hydrochloride) which is suitable for once-daily oral administration. The formulation of the present invention comprises a quantity of a quick release preparation of diltiazem or a pharmaceutically active salt thereof, mixed with a quantity of a slow release (or delayed release) preparation of diltiazem or a pharmaceutically active salt thereof. The quick release preparation used obtains a maximal release of diltiazem within approximately 1–2 hours after administration, and then falls toward baseline levels. The delayed release preparation individually shows a maximal release of diltiazem at between approximately 6–8 hours after administration. The extended release formulation of the present invention is characterized by its' rapidly releasing diltiazem or its pharmaceutically acceptable salt, the rapid release characterized by obtaining a maximal release of diltiazem or its pharmaceutically active salt approximately within 1–2 hours after administration, and the extended release formulation is further characterized by its maintaining the released diltiazem or pharmaceutically active salt thereof at almost maximal levels over a period of approximately 12 hours after achieving the maximum release. In its preferred embodiment, the present invention is a capsule containing the extended release formulation, which, based upon the total quantity of drug in the formulation rather than total weight of the formulation, comprises up to approximately 25 percent by weight of the quick release preparation of diltiazem, and up to 75 percent by weight of the slow (or delayed) release preparation of diltiazem.

DETAILED DESCRIPTION OF THE INVENTION

Introduction

Figure 1A:
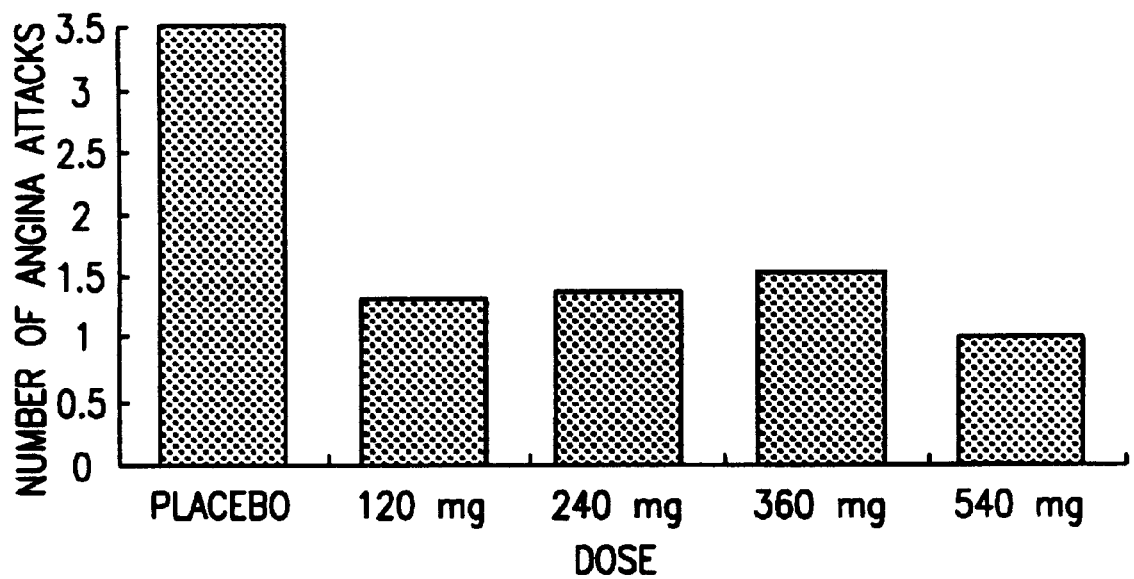
FIG. 1A illustrates the dose response of patients treated with differing dosages of Diltiazem OD ER, an extended (or slow) release preparation of diltiazem hydrochloride.

Diltiazem ((25-cis-3-(Acetoxyl)-5-[2-(dimethylamino)ethyl]-2-3-dihydro-2-(4-methoxyphenyl)-1,5-benzothiazepin-4(5H)-one) (1) is a safe and effective treatment for both stable and unstable angina pectoris. With regard to efficacy, diltiazem has been reported to be equivalent to beta-andrenergic receptor blockers (5–9), nitrates (5,6) and verapamil (alpha-[3-[[2-(3,4-Dimethoxyphenyl)ethyl]methylamino]propyl]-3,4[dimethoxy-alpha-(1-methylethyl)-benzeneacetonitrile (10)(11,12) and more effective than nifedipine (1,4-Dihydro-2,6-dimethyl-4-(2-nitrophenyl)-3,5-pyrdinecarboxylic acid dimethyl ester) (13) (14,15). Although comparative studies demonstrated equivalent the anti-anginal effects for many of the calcium channel blockers on the market, these studies have shown a lower incidence of side effects with diltiazem (16). Consequently, diltiazem is a frequently prescribed medication and the world wide market for it exceeds $1 billion As used in the context of this specification, the extended release formulation of diltiazem hydrochloride marketed as CARDIZEM CD (TM) may be referred to as Diltiazem CD, and referred to as a slow or delayed release preparation of diltiazem.

DILACOR XR (TM), an extended release formulation of diltiazem hydrochloride will also be referred to as Diltiazem ER (extended release), and referred to as a slow or delayed release preparation of diltiazem.

Diltiazem OD ER (Once-a-Day, Extended Release as described in the literature) is an extended release formulation of diltiazem and may also be referred to as a slow or delayed release preparation of diltiazem.

Metabolic studies have shown that diltiazem, like other calcium channel blockers, undergoes extensive first pass metabolism by the liver, with a plasma half-life in the range of 2–6 hours (17,19). Briefly, first-pass metabolism refers to the rapid metabolism of a drug in the liver after a substantial portion of the absorbed dose has been extracted from the blood. This results in a significant decrease in the bioavailability of the drug, often as much as a 60% loss. Thus, a single oral dose of an immediate release preparation (or formulation) of diltiazem must be administered 3–4 times per day to provide adequate control of hypertension or angina (20–22). A problem associated with this dosing regimen is that patient compliance is often very low (23). Further, many of the side effects noted with some of the immediate release formulations of diltiazem result from the high peak levels of the drug that occur in the plasma prior to complete distribution.

In an effort to provide therapeutic blood levels of diltiazem for longer periods of times and to improve patient compliance, several slow-release or extended-release formulations of diltiazem have been developed for treatment of hypertension (24–26) and angina (27–30). Such sustained release formulations may provide adequate therapeutic blood levels during the patient's sleeping hours and upon waking in the morning, in addition to better patient compliance.

Figure 1B:
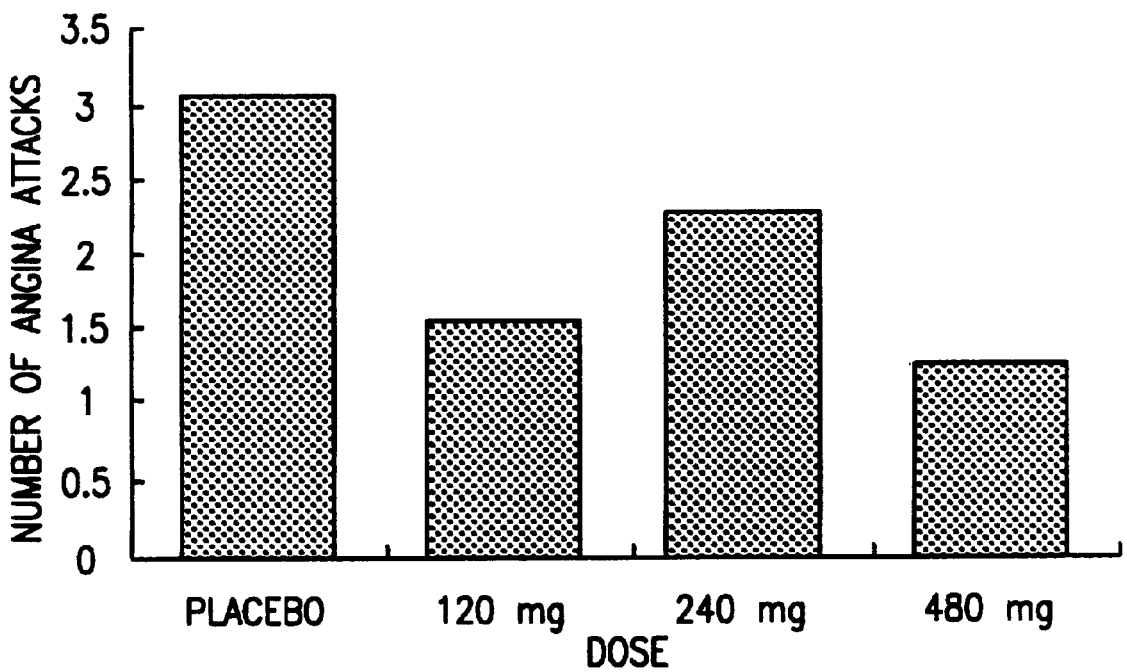
FIG. 1B illustrates the dose response of patients treated with differing dosages of Diltiazem XR (TM), an extended (or slow) release preparation of diltiazem hydrochloride.

Analysis of the anti-anginal effects of the three major once-daily, extended release formulations of diltiazem reveals that all three preparations only produce a partial reduction in angina. As shown in FIG. 1, Diltiazem OD ER and Diltiazem XR all maximally reduce the number of angina attacks by approximately 50–60% regardless of how high a dose is given. Both Diltiazem OD ER (FIG. 1A) and Diltiazem XR (FIG. 1B) reduced angina attacks at a dose of 120 mg, but no further effects were seen at doses as high as 540 mg. The data for Diltiazem CD are not shown, but have been reported to be similar (28). These residual angina attacks can be very uncomfortable for the patients, and have the more serious potential for becoming life-threatening.

Figure 2:
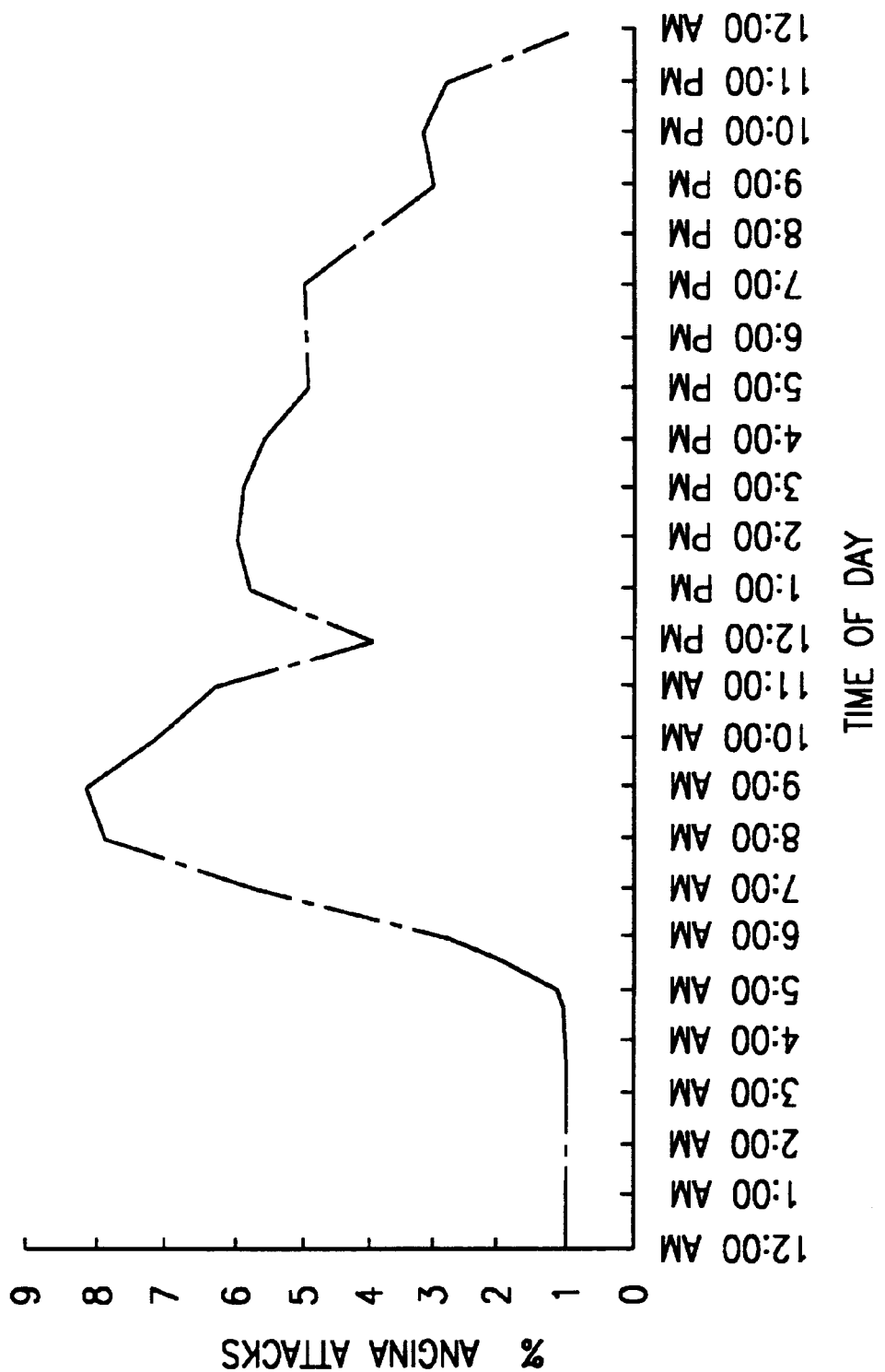
FIG. 2 shows the circadian rhythm of angina attacks observed in patients over a 24 hour time period.

Analysis of the chronobiology of angina attacks in relation to the pharmacokinetics of these drugs can resolve this particular deficiency of the once-daily, extended release formulations of diltiazem. A diurnal rhythm for angina attacks has been reported, with approximately 40–50% of these attacks occurring between 6:00 AM and noon (31,32). FIG. 2 illustrates data from Taylor et al. (31), where practically all of the attacks occurred during the waking hours, and occurred in two distinct phases. The first phase occurred in the morning beginning at approximately 6:00 AM and reaching a peak between approximately 8:00 AM and 10:00 AM. The second phase began at approximately 1:00 PM and lasted approximately 8 hours. Other studies have shown the occurrence of similar diurnal rhythms for myocardial infarction (33), ischemic ST segment depression (34) and sudden cardiac death (35). These studies suggest that it is critical to achieve proper medication levels during the morning hours where a significant amount of abnormal cardiac activity occurs.

Figure 3:
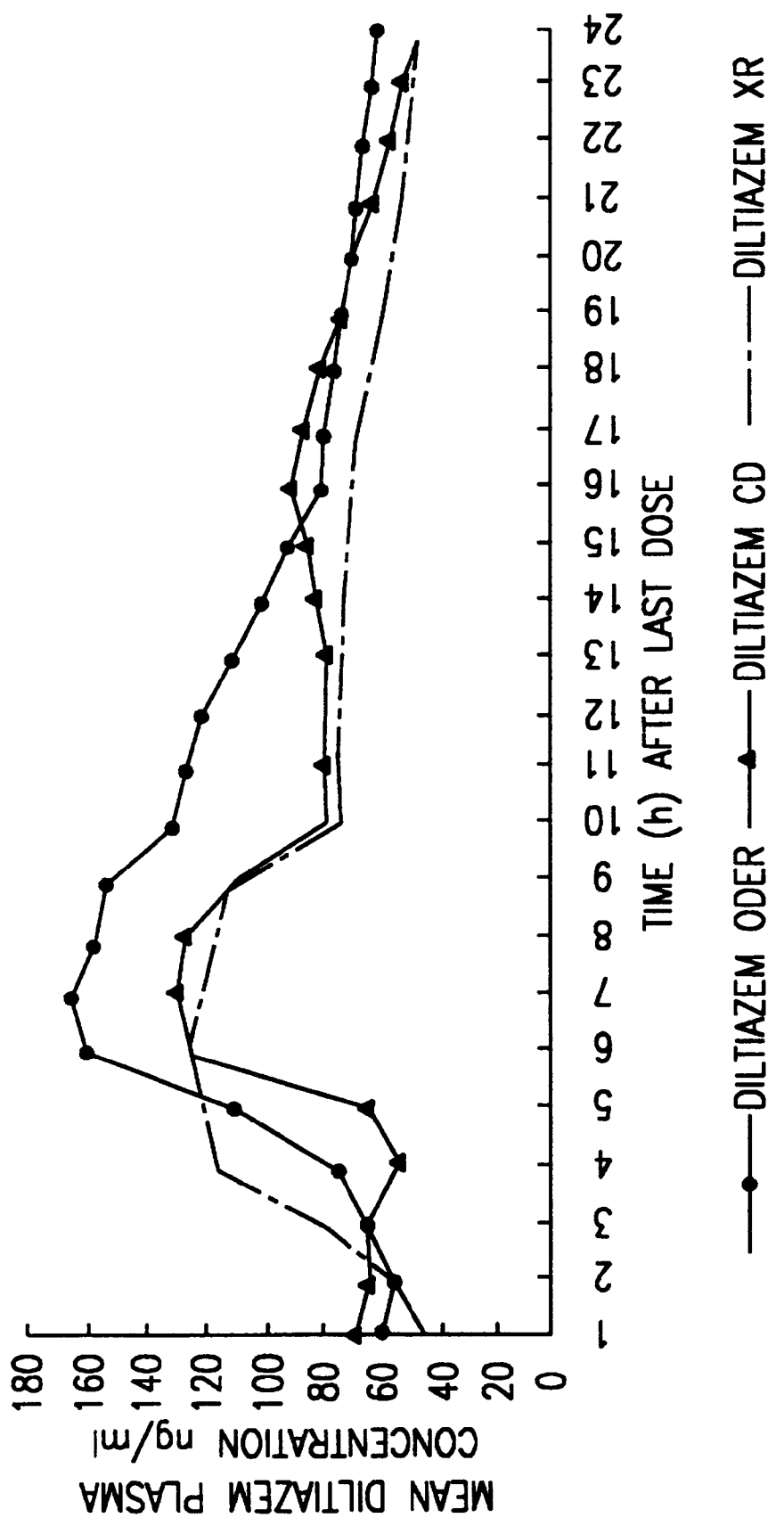
FIG. 3 shows the plasma levels of diltiazem hydrochloride obtained after individuals were given one of three different extended (or slow) release preparations of diltiazem hydrochloride over an eight day time period.
Figure 4:
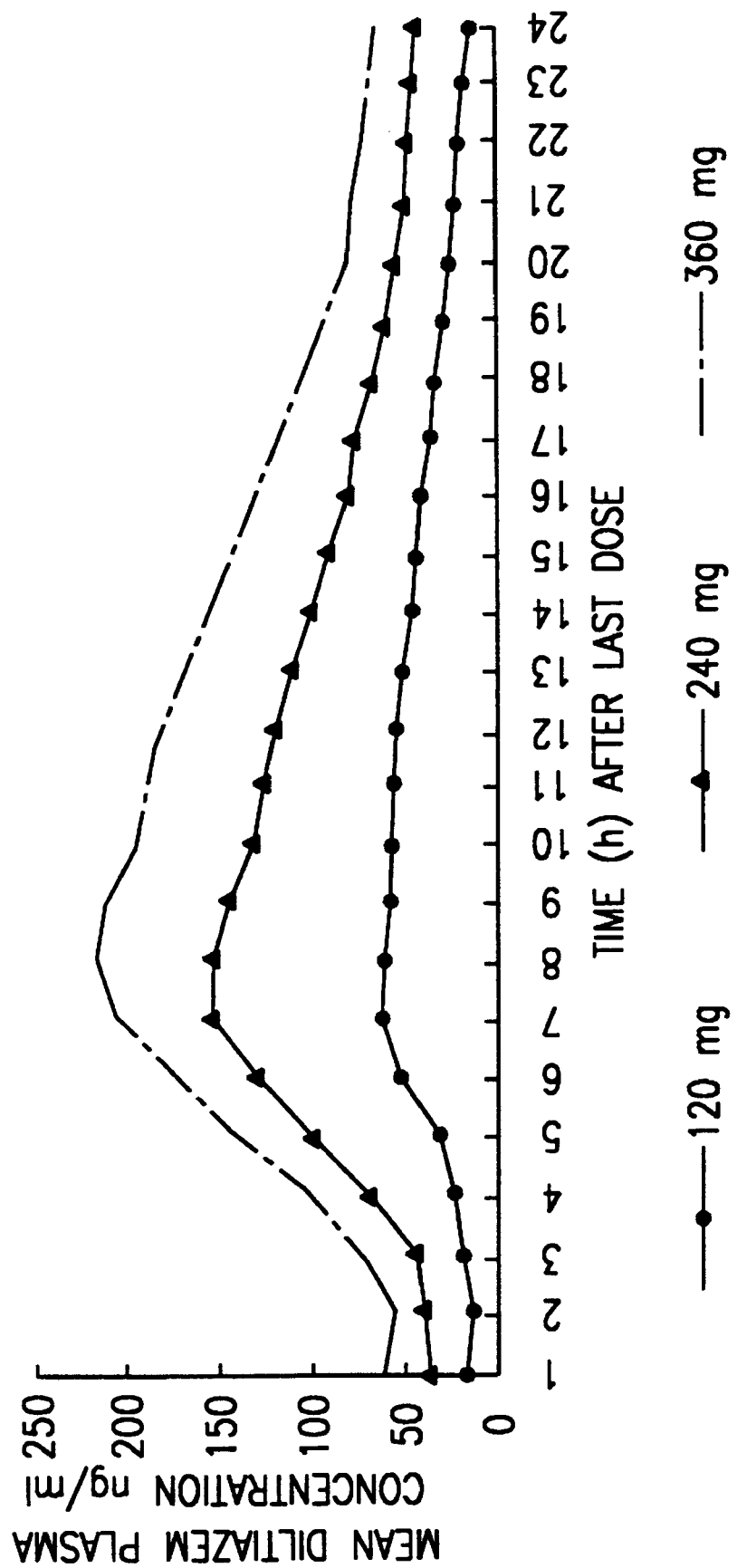
FIG. 4 shows the plasma levels of diltiazem hydrochloride obtained after individuals were given different concentrations of an extended (or slow) release preparation of diltiazem hydrochloride (Diltiazem OD XR) over an eight day time period.

Extended release formulations of diltiazem are generally taken in the morning. Diltiazem is slowly released from these formulations and slowly absorbed, in order to provide an extended and long-lasting dosage. Thus, by their very nature, these once-daily extended release formulations of diltiazem are unable to provide this morning medication. Plasma levels of Diltiazem OD ER, Diltiazem CD (CARDIZEM CD) and Diltiazem XR (DILACOR XR) increase slowly and reach peak levels only after 4–6 hours after ingestion, even though these drugs had been administered to the patients for 8 eight days prior to the last dose of the drug (FIG. 3). Thus, for drugs taken at 8:00 AM, peak plasma levels are not reached until approximately 12:00 Noon and 2:00 PM. This slow absorption of diltiazem is not altered by increasing the dosage. In the study whose results are shown in FIG. 4, patients in three groups were given different doses of Diltiazem OD ER. Although the peak plasma levels were increased with the increased dosage of drug, the time needed to obtain those peak levels remained relatively constant, being approximately 7 hours. These data suggest that once-daily, extended release formulations of diltiazem, if administered upon waking, are unable to provide sufficient plasma levels of drug when their presence is necessary, in the morning.

Figure 5:
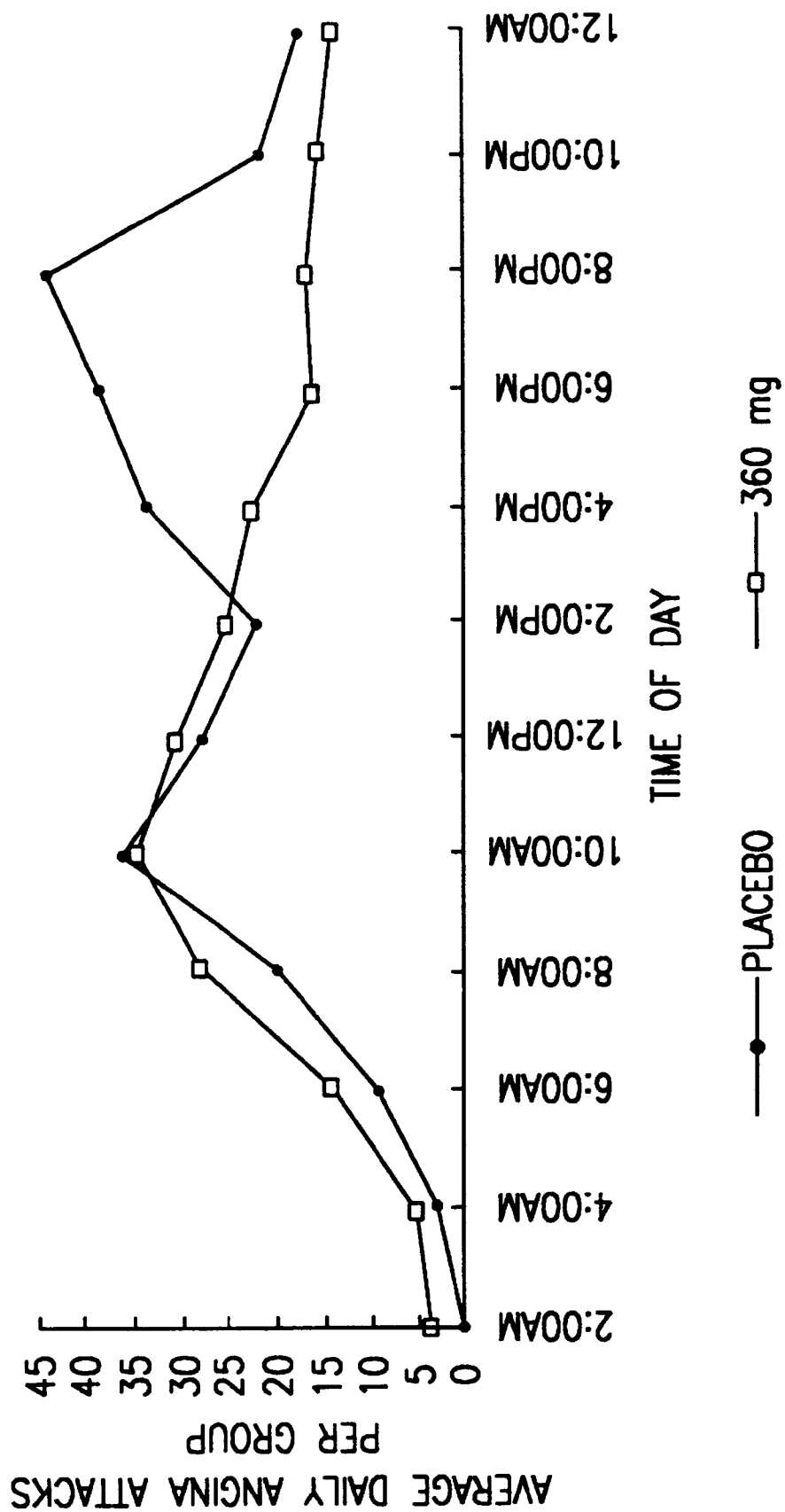
FIG. 5 shows the diurnal rhythm of anginal attacks of individuals given a placebo and 360 mg of Diltiazem OD ER over a two week time period.

The importance of achieving sufficient plasma levels in the morning is further highlighted by data shown in FIG. 5. In this unpublished study, patients were administered Diltiazem OD ER at approximately 8:00 AM daily for a two week period, and were asked to record the time of day at which angina attacks occurred. Diltiazem OD ER did not reduce angina attacks until well into the afternoon (approximately 4:00 PM and later), once peak plasma levels were attained; morning angina attacks were unaffected. This data may explain why the once-daily extended release formulations of diltiazem do not completely suppress angina attacks.

Results and Discussion

The present invention is described in Example 1 below.

EXAMPLE 1

The contents of two 180 mg capsules of DILACOR XR (TM) were emptied, yielding 360 mg of diltiazem hydrochloride. This preparation was mixed with 120 mg of diltiazem hydrochloride. DILACOR XR (TM) is an extended release formulation of diltiazem hydrochloride, as described earlier (3) and will be referred to here as a slow release (or delayed release) preparation of diltiazem. Diltiazem hydrochloride is the immediate release formulation of diltiazem, and will be referred to here as a quick release preparation of diltiazem.

One hundred twenty milligrams (120 mg) of diltiazem hydrochloride powder were mixed with 360 mg of DILACOR XR (TM), producing an extended release formulation of diltiazem hydrochloride. Because many pharmaceutical excipients are used in the formulation of DILACOR XR (TM), the weight of the contents of a capsule is therefore greater than the weight of the drug contained therein. Therefore, as will be described below, the weight percentages described are based upon the percent weight of the drug in the preparation (i.e., whether the quick release or the slow release preparation) in relation to the quantity of the active drug in the mixture. Consequently, this mixture contained approximately 25 percent by weight of a quick release preparation of diltiazem, and approximately 75 percent by weight of a slow release preparation of diltiazem, based upon the percentage of diltiazem in the final mixture. An individual capsule of DILACOR XR (TM) contains two tablets, representing its multiple diltiazem components, as described in the Physician's Desk Reference (3).

The resulting mixture was then encapsulated in a larger gelatin capsule and orally administered to a healthy individual, taking no medications which would affect diltiazem plasma levels or interfere with their proper determination. Controls containing either 120 mg diltiazem hydrochloride or 360 mg Diltiazem ER were administered separately. An interval of approximately 5–7 days elapsed between the administration of each agent tested in this example.

An intravenous blood sample was withdrawn into pre-cooled, commercially available VACUTAINERS (TM) containing EDTA (ethylenediamine tetraacetic acid) as an anticoagulant just before administration of the test agent; this sample represented the zero time sample. The blood sample was centrifuged for 15 minutes under conditions known to those skilled in the art. The plasma portion of each sample was harvested, frozen and stored at minus 70 degrees Celsius until analysis. At timed intervals after administration, additional blood samples were withdrawn and similarly treated. The plasma levels of diltiazem were determined by HPLC (High Performance Liquid Chromatography) analysis according to the method of Eradiri (36).

Figure 6:
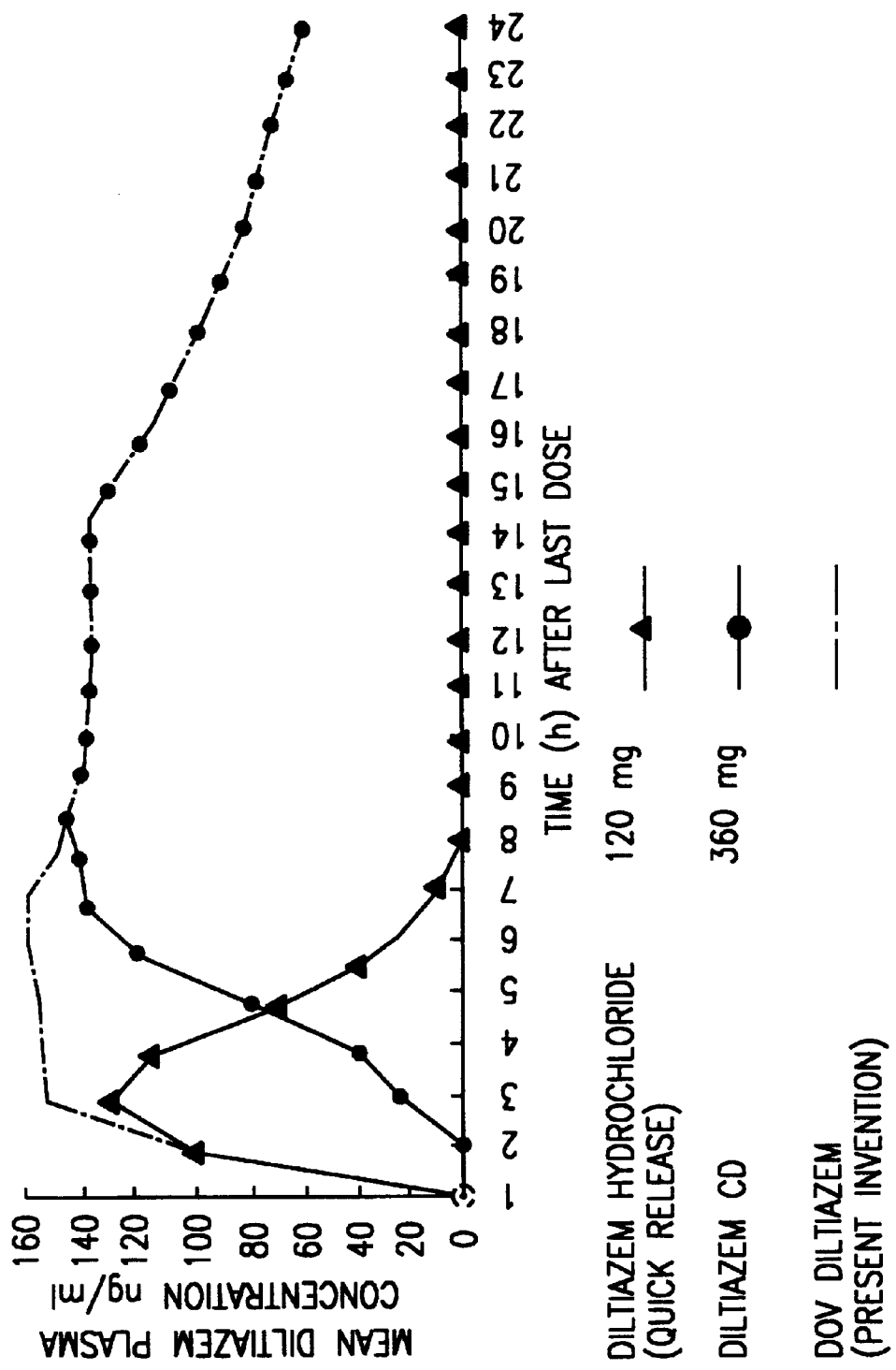
FIG. 6 shows the plasma levels obtained using the present invention (squares), and with separate doses of the individual components of the present invention (circles and triangles).

As shown in FIG. 6, peak plasma levels of diltiazem were reached between approximately 1–2 hours after administration of diltiazem hydrochloride, the immediate release formulation (quick release preparation) (triangles). Most of the quick release preparation is gone by approximately 5–6 hours after administration. Diltiazem XR, the extended release formulation (or slow release preparation) individually, reached peak plasma levels after approximately 6–7 hours after administration, and maintained these peak levels for approximately another 10–12 hours. The formulation of the present invention (squares) achieved peak plasma levels within approximately 2 hours after administration, and maintained those peak levels for approximately 6 hours, during which time plasma levels of individually administered diltiazem hydrochloride decreased and during which time the plasma level of individually administered Diltiazem XR was increasing and reaching its peak plasma level. The plasma levels of the formulation of the present invention were sustained for approximately 16 hours before they began to decline.

Most angina attacks have been shown to occur within the first 2 hours after waking. The present invention achieves its maximal release of diltiazem within two hours after oral administration, and maintains almost the peak diltiazem levels for an extended time period thereafter, the present invention can provide complete coverage both in the morning and in the afternoon to achieve a maximum suppression of angina attacks. Further, based on the pharmacokinetics shown in FIG. 6, a somewhat constant level of diltiazem is sustained throughout the day, eliminating major fluctuations in blood levels (i.e., blood plasma levels).

As described in the literature, the extended release formulations of diltiazem or diltiazem hydrochloride contain diltiazem along with various pharmaceutical excipients, such as binders or other inert ingredients, on a pharmaceutically acceptable inert core or seed. Any of the binding agents known to those skilled in the art can be utilized, such as, but not meant to be limited to, starch or other sugars. Other pharmaceutical excipients which may be utilized in formulating the slow release preparation include, but are not meant to be limited to, talc, stearates, acidifying agents where necessary, preservatives such as antimicrobial compounds, etc. These excipients may further include a lubricant selected from among waxes, castor oil, mineral oil, and others.

The coating agents used to form the slow release preparation can be selected from a variety of compounds known to those skilled in the art. For example, the formulation of Hendrickson et al. in U.S. Pat. No. 5,286,497 employs a polymeric coating using polymerized acrylate compounds, although they describe that one of a number of other such compounds can be used. The formulation described by Geoghegen et al. in U.S. Pat. No. 4,917,899 similarly employs a coating prepared from acrylate polymers to effect the slow release of diltiazem from the core. Methods of encapsulating or tableting these preparations are also known to those skilled in the art. The capsules can be either a hard or soft gelatin capsule.

The terms "agent", "drug", "pharmaceutical", or "pharmaceutically active compound", have been used interchangeably when referring to the compound being released from the formulation. These compounds can include those which act on various organs of the body, antibiotics, other antimicrobials, beta-blockers, calcium channel blockers, neurological agents, etc.

All of the references cited in this specification are hereby incorporated by reference to the extent pertinent.

The formulation and its applications described in the present invention is not intended to be limited to those embodiments illustrated in the Examples, but only to the extent described in the following Claims.

REFERENCES CITED

1. Merck and Co., Inc. Diltiazem. Merck Index 1996, 12th ed. No. 3247, p. 3249.
2. Marion Merrill Dow. Cardizem (TM) CD Capsules. Physician's Desk Reference. 1995. 49th ed. 1399.
3. Rhone-Poulenc Rorer. Dilacor XR. Physician's Desk Reference. 1995. 49th ed. 1966.
4. Forest Pharmaceuticals, Inc. Tiazac. Physician's Desk Reference. 1998, 52nd ed. 957–959.
5. Cohn, P. F., Concomitant use of nitrates, calcium channel blockers, and beta-blockers for optimal antianginal therapy. Clin. Cardiol. 1994 17:415–421.
6. Chan, P. K., Heo., J. Y., Garibian, G. et al., The role of nitrates, beta blockers, and calcium antagonists in stable angina pectoris. Am. Heart J. 1988 116:838–848.
7. Humen, D. P., O'Brien, P., Purves, P., et al, Effort angina with adequate beta-receptor blockade: comparison with diltiazem alone and in combination. J. Am. Coll. Cardiol. 1986 7:329–335.
8. Kenny, J., Kiff, P., Holmes, J. et al., Beneficial effects of diltiazem and propranolol, alone and in combination, in patients with stable angina pectoris. Br. Heart J. 1985 53:43–46.
9. Kostuk, W. J., Pflugfelder, P. Comparative effects of calcium entry-blocking drugs, and their combination in patients with chronic stable angina. Circulation 1987 75:V114–121.
10. Merck & Co., Inc. Verapamil. Merck Index 1996 12th ed. No. 10083, p 1696.
11. Belin, A., Grien, P., Mabire, J. P., et al., [Comparison of the efficacy of verapamil and diltiazem in stable exercise angina. A double-blind and crossover study]. Arch. Mal. Coeur Vaiss 1990 83:393–398. (In French)

12. Chaffman, M., Brogden, R. N. Diltiazem. A review of its pharmacological properties and therapeutic efficacy. Drugs 1985 29:387–454.
13. Merck & Co., Inc. Nifedipine. Merck Index 1996 12th ed. No. 6617, p 1121.
14. Bory, M., Gillet, T., Bonnet, J. L., et al., [Comparative study of effects of diltiazem, nifedipine and their combination on exercise stable angina.] Arch. Mal. Coeur Vaiss 1991 84:235–242. (In French)
15. Frishman, W., Charlap, S., Kimmel, B., et al., Diltiazem, nifedipine, and their combinations in patients with stable angina pectoris: effects on angina, exercise tolerance, and the ambulatory electrocardiographic ST segment. Circulation 1988 77:774–786.
16. Opie, L. H. Calcium channel antagonists. Part II: Use and comparative properties of the three prototypical calcium antagonists in ischemic heart disease, including recommendations based on an analysis of 41 trials. Cardiovasc. Drugs Ther. 1988 1:464–491.
17. Hoglund, P., Nilsson, L. G. Pharmacokinetics of diltiazem and its metabolites after repeated multiple-dose treatments in healthy volunteers. Ther. Drug Monit. 1989 11:543–550.
18. Bianchetti, G., Regazzi, M., Rondanelli, R., et al. Bioavailability of diltiazem as a function of the administered dose. Biopharm. Drug Dispos. 1991 12:391–401.
19. Boyd, R. A., Chin, S. K., Don-Pedro, O. et al. The pharmacokinetics and pharmacodynamics of diltiazem and its metabolites in healthy adults after a single oral dose. Clin. Pharmacol. Ther. 1989 46:408–419.
20. Bala Subramanian, V., Khurmi, N. S., Bowles, M. J., et al. Objective evaluation of three dose levels of diltiazem in patients with chronic stable angina. J. Am. Coll. Cardiol. 1990 1:1144–1153.
21. Boman, K., Saetre, H., Karlsson, I. G. et al. Antianginal effect of conventional and controlled release diltiazem in stable angina pectoris. Eur. J. Clin. Pharmacol. 1995 49:27–30.
22. McCans, J. L. Diltiazem dose responses in sustained therapy for stable angina pectoris. Can. J. Cardiol. 1986 2:332–337.
23. Farmer, K. C., Jacobs, E. W., Phillips, C. R. Long-term patient compliance with prescribed regimens of calcium channel blockers. Clin. Ther. 1994 16:316–326.
24. Lacouriere, Y., Poirier, I, Lefebvre, J., et al. Clinical efficacy of force titrated doses of diltiazem extended-release. A placebo controlled study. Am. J. Hypertension 1995 8:282–286.
25. Guimont, S., Landriault, H., Klischer, K. et al. Comparative pharmacokinetics and pharmacodynamics of two marketed bid formulations of diltiazem in healthy volunteers. Biopharm. Drug Dispos. 1993 14:767–778.
26. Dupont, A., Coupez, J., Jensen, P., et al. Twenty-four hour ambulatory blood pressure profile of a new slow-release formulation of diltiazem in mild to moderate hypertension. Cardiovasc. Drugs Ther. 1991 5:701–708.
27. Cutler, N., Eff, J., Fromell, G., et al. Dose-ranging study of a new, once daily formulation for patients with stable angina. J. Clin. Pharmacol. 1995 35:189–195.
28. Thadani, U., Glasser, S., Bittar, N., et al. Dose-response evaluation of once-daily therapy with a new formulation of diltiazem for stable angina pectoris. Diltiazem CD Study Group.—Am. J. Cardiol. 1994 74:9–17.
29. Weiner, D., Cutler, S., Klein, M. Efficacy and safety of sustained-release diltiazem in stable angina pectoris. Am. J. Cardiol. 1986 57:6–9.
30. Khinke, W. P., Baird, M., Juneau, M., et al. Antianginal efficacy and safety of controlled delivery diltiazem QD versus an equivalent dose of immediate release diltiazem TID. Cardiovasc. Drugs Ther. 1995 9:319–330.
31. Taylor, C., Hodge, E., White, D. Circadian rhythm of angina: similarity to circadian rhythms of myocardial infarction, ischemic ST segment depression and sudden cardiac death. Am. Heat J. 1989 118:1098–1099.
32. Mulcahy, D., Keegan, J., Crean, P., et al. Select myocardial ischemia during ambulatory electrocardiographic monitoring in patients with effort angina. Am J. Med. 1988 81:2–6.
33. Muller, J., Stone, P., Turi, Z., et al., Circadian variation in the frequency of onset of acute myocardial infarction. N. Engl. J. Med. 1985 313:1315–1322.
34. Rocco, M., Brry, J., Campbell, S. et al. Circadian variation of transient myocardial ischemia in patients with coronary artery disease. Circulation 1987 75:395–400.
35. Muller, J., Ludmer, P., Willich, S. et al. Circadian variation in the frequency of sudden cardiac death. Circulation 1987 75:131–138.
36. Eradiri, O., and Midha, K. K. Use of parent drug and metabolite data in bioavailability assessment of a novel diltiazem hydrochloride once-daily product. Pharmaceutical Research 1995 12:2071–2074.

What is claimed is:

1. An extended release pharmaceutical formulation comprising:
   a. a pharmaceutically active compound or a pharmaceutically active salt thereof in the amount of between 1% to 25% of total weight of the active compound; and
   b. a quantity of between 75% to 99% of the total weight of the active compound of a preparation of a pharmaceutically active compound or a pharmaceutically active salt thereof wherein the preparation is characterized by a delayed release of the pharmaceutically active compound or the pharmaceutically active salt thereof with a maximum release of the active compound or active salt thereof achieved within approximately 5–8 hours of administration.

2. The controlled release formulation as described in claim 1, wherein the quantity of the pharmaceutically active compound or the pharmaceutically active salt thereof achieves a maximum release of the active compound or active salt thereof within approximately 1–2 hours of administration.

3. The controlled release formulation as described in claim 1, wherein the controlled release formulation maintains the released active compound or active salt thereof at almost the maximum levels over a period of approximately 12 hours after achieving the maximum release.

4. The controlled release formulation as described in claim 3, wherein the controlled release formulation is suitable for once-daily administration.

5. The controlled release formulation as described in claim 3, wherein the formulation is suitable for oral administration.

6. The controlled release formulation as described in claim 5, wherein the release of the active compound or its active salt thereof is measured by determining the concentration of the released active compound or its active salt thereof in the blood plasma.

7. The controlled release formulation as described in claim 5, wherein the pharmaceutically active compound consists of diltiazem, or a pharmaceutically active salt thereof, and the pharmaceutically active compound in the preparation is diltiazem or a pharmaceutically active salt thereof.

8. A capsule comprising an controlled release formulation according to claim 1.

9. A extended release diltiazem formulation, comprising:
a. diltiazem or a pharmaceutically active salt thereof in the amount of between 1% to 25% of total weight of the active compound; and
b. a quantity of between 75% to 99% of the total weight of the active compound of a preparation of diltiazem or a pharmaceutically active salt thereof wherein the preparation is characterized by a delayed release of the diltiazem or the pharmaceutically active salt thereof with a maximum release of the active compound or active salt thereof achieved within approximately 5–8 hours of administration.

10. The controlled release diltiazem formulation as described in claim 9, wherein the quantity of diltiazem or the pharmaceutically active salt thereof achieves a maximum release of diltiazem or the active salt thereof within approximately 1–2 hours.

11. The controlled release diltiazem formulation as described in claim 9, wherein the controlled release formulation maintains the released diltiazem or pharmaceutically active salt thereof at almost maximum levels over a period of approximately 12 hours after achieving the maximum release.

12. The diltiazem formulation as described in claim 11, wherein the controlled release diltiazem formulation is suitable for once-daily administration.

13. The controlled release diltiazem formulation as described in claim 11, wherein the controlled release diltiazem formulation is suitable for oral administration.

14. The controlled release diltiazem formulation as described in claim 13, wherein the release of diltiazem or its pharmaceutically active salt thereof is characterized by determining the concentration of diltiazem or its pharmaceutically active salt thereof in blood plasma.

15. A capsule comprising an controlled release diltiazem formulation of diltiazem or a pharmaceutically acceptable salt thereof according to claim 9.

16. A method for producing an extended release formulation of diltiazem, comprising:
a. obtaining a quantity of diltiazem or a pharmaceutically active salt thereof of between 1% to 25% of total weight of the active compound,
the diltiazem or the pharmaceutically active salt thereof achieving a maximum release of diltiazem or the pharmaceutically active salt thereof within approximately 1–2 hours;
b. obtaining a quantity of a preparation of diltiazem or a pharmaceutically active salt thereof of between 75% to 99% of the total weight of the active compound,
the preparation of diltiazem or the pharmaceutically active salt thereof achieving a maximum release of diltiazem or the pharmaceutically active salt thereof within approximately 5–8 hours; and
c. mixing the diltiazem or the pharmaceutically active salt thereof together with the preparation to form the extended release formulation, wherein the extended release formulation is characterized by rapidly releasing diltiazem or its pharmaceutically active salt thereof, the rapid release characterized by obtaining a maximum release of diltiazem or its active salt within approximately 1–2 hours after administration, and wherein the extended release diltiazem formulation is further characterized by its maintaining the released diltiazem or pharmaceutically active salt thereof at almost maximum levels over a period of approximately 12 hours after achieving the maximum release.

* * * * *

UNITED STATES PATENT AND TRADEMARK OFFICE
CERTIFICATE OF CORRECTION

PATENT NO. : 6,162,463　　　　　　　　　　　　　　　　　　　　　　　　Page 1 of 1
DATED : December 19, 2000
INVENTOR(S) : Arnold S. Lippa It is certified that error appears in the above-identified patent and that said Letters Patent is hereby corrected as shown below:

<u>Title page,</u>
Insert the following:

Assignee: DOV Pharmaceutical Incorporated
　　　　　　 Fort Lee, New Jersey

Signed and Sealed this

Eighteenth Day of December, 2001

Attest:

Attesting Officer

JAMES E. ROGAN
*Director of the United States Patent and Trademark Office*